United States Patent [19]

Balenseifen

[11] Patent Number: 4,571,179
[45] Date of Patent: Feb. 18, 1986

[54] ORTHODONTIC APPLIANCE

[76] Inventor: Jack W. Balenseifen, 7505 NW. 23, Bethany, Okla. 73008

[21] Appl. No.: 722,039

[22] Filed: Apr. 11, 1985

[51] Int. Cl.⁴ .............................................. A61C 3/00
[52] U.S. Cl. ........................................ 433/20; 433/22
[58] Field of Search ......................... 433/20, 22, 23, 7

[56] References Cited

U.S. PATENT DOCUMENTS

| | | | |
|---|---|---|---|
| 3,178,822 | 4/1965 | Fogel et al. | 433/20 |
| 3,600,808 | 8/1971 | Reeve | 433/20 |
| 3,792,529 | 2/1974 | Goshgarian | 433/7 |
| 4,202,100 | 5/1980 | Forster | 433/7 |
| 4,268,250 | 5/1981 | Reeve | 433/20 |
| 4,318,694 | 3/1982 | Klein | 433/22 |

Primary Examiner—John J. Wilson
Attorney, Agent, or Firm—Robert K. Rhea

[57] ABSTRACT

An orthodontic arch wire is arcuately curved in the plane of a patient's mandibular dental arch. Respective end portions of the arch wire are offset inwardly for connection with cuspid surrounding orthodontic bands or bonding pads. The arch wire is provided with one or a plurality of selectively positioned transverse closed loops formed by doubling the wire back upon itself to extend in a lingual direction angled downwardly at an angle of 40° to 60° with respect to a plane normal to the plane of the arch wire permitting the arch wire to be flexed away from the patient's teeth against the torsional resistance normally applied to the teeth by the arch wire. The wire flexing feature permits applying one or more tooth position correcting split sleeves to the arch wire.

7 Claims, 6 Drawing Figures

ORTHODONTIC APPLIANCE

BACKGROUND OF THE INVENTION

1. Field of the Invention

This invention relates to orthodontics retention and particularly to an adjustable retainer which is united to the teeth by a fixed orthodontic band or a direct bond pad.

The need for such an orthodontic adjustable retainer arises from the factor that most patients after completing orthodontic treatment will not wear their removable retainers; consequently, the patient's teeth will shift and may become unhealthy. The increasing demands on an orthodontist make it desirable to provide a means for treating and satisfactorily completing more patients in less time and obtaining excellent long term retention of an excellent occlusion. The appliance of this invention is simple and uniform in structure so that laboratory technicians and other auxiliary personnel can prefabricate the appliance in the laboratory.

From a therapeutic standpoint, a fixed orthodontic adjustable retainer should be able to correct minor tooth irregularities. The appliance must be capable of effecting desired changes in the mandibular cuspids and/or mandibular incisors with minimal disturbance of the rest of the teeth. The adjustable retainer, when bonded or cemented to the teeth, should also be a natural "power source" from which energy can be derived in order to correct minor labial-lingual position, rotations, intrusions, and extrusions of the mandibular cuspids and incisors. The introduction of a light, gentle force via this retainer is consistent with physiological response of the teeth to a light, gentle force which is preferable to heavier forces.

2. Description of the Prior Art

Fixed nonadjustable orthodontic retainers are in common use by orthodontists, and they are used for the retaining (holding) of teeth after they have been correctly aligned. The popular mandibular fixed orthodontic retainer is in the form of a circular arched wire attached at its respective ends to two orthodontic bands. The wire is continuous (no breaks or loops) from the lingual side of one cuspid band or bonding pad to the lingual side of the other cuspid band or pad. The main disadvantages of the popular fixed continuous cuspid to cuspid retainers are: (1) It cannot be adjusted. (2) It must be constructed with the utmost accuracy or it will not fit correctly on the abutment teeth. (3) It will not correct minor irregularities. (4) No change in style in 30-40 years.

This easily installed and adjusted appliance can save many valuable working hours for the orthodontist and time for the patient, and eliminate a lot of retreating of orthodontic cases because of minor irregularity in the mandibular incisor-cuspid areas. Since the appliance is banded or bonded to the teeth, the patient is less likely to lose or destroy it. The appliance is very durable and sanitary, and causes a minimum of discomfort to the patient.

SUMMARY OF THE INVENTION

A length of orthodontic wire is arcuately curved to define an arch conforming to the preferred arch of cuspid and incisor teeth of a patient to be treated. The respective end portions of the wire are laterally offset inwardly to facilitate their connection, in a conventional manner, with an orthodontic band or direct bond pad surrounding or secured to cuspids. Intermediate its length, the wire is doubled back upon itself to form at least one and not more than three transverse closed loops extending in a lingual direction at an angle of 40° to 60° with respect to a plane normal to the plane of the arched wire.

The principal objects of this invention are to provide a new and improved adjustable orthodontic retaining appliance; may be used for several orthodontic retaining therapies for extremely small detailed, precise movement of teeth; and may be inserted and adjusted as needed to accomplish easily and quickly all minor tooth movements requiring a minimum of time by the orthodontist to properly treat the patient in his office.

A further object of this invention is to provide an orthodontic adjustable retainer that can be uniformly partially preassembled, and when completely assembled in the laboratory, it can be inserted precisely, rapidly, and painlessly on the teeth to save valuable time for the orthodontist and the patient.

DESCRIPTION OF THE PREFERRED EMBODIMENTS

Figure 1:
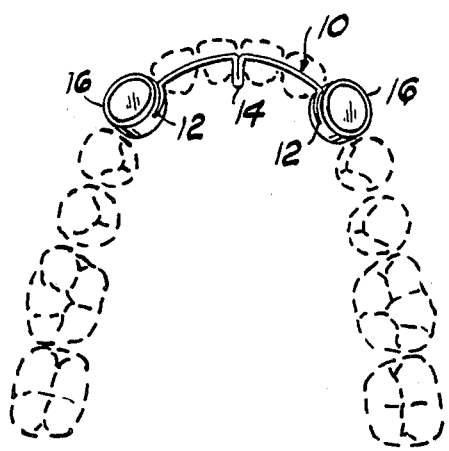
FIG. 1 is a top view of one embodiment of the device when installed on a patient's teeth, the latter being shown by dotted lines.

Like characters of reference designate like parts in those figures of the drawings in which they occur.

Figure 3:
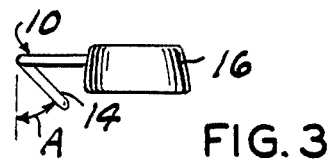
FIG. 3 is a side elevational view of the device shown by FIGS. 1 and 2, per se.
Figure 4:
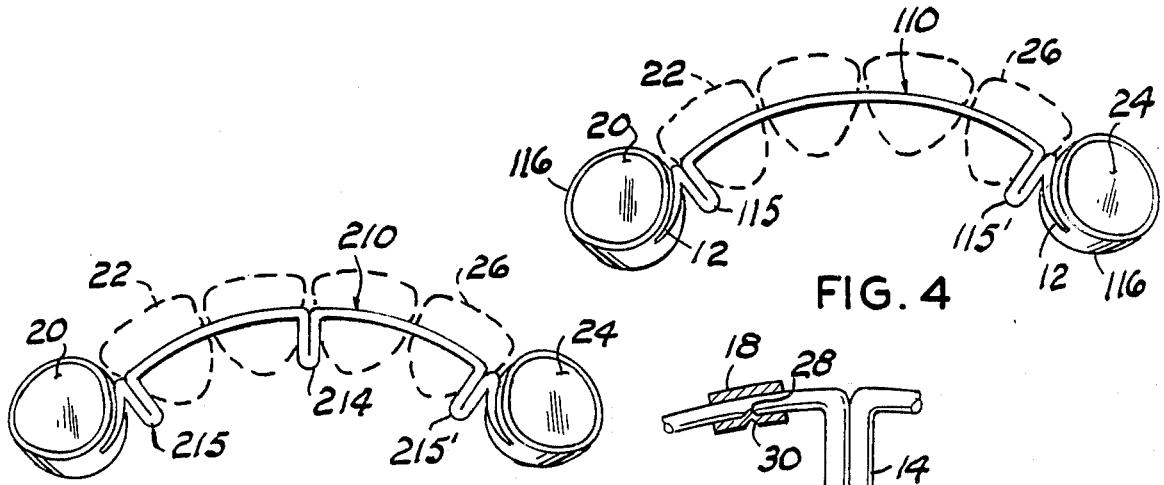
FIGS. 4 and 5 are top views similar to FIG. 2 illustrating other embodiments of the device; and, FIG. 6 is a fragmentary view, to a further enlarged scale, partially in section, illustrating the manner of securing a tooth position adjusting sleeve to the device.

In the drawings:

The reference numeral 10 indicates a transverse fixed position orthodontic adjustable retainer. I prefer to make the fixed position orthodontic adjustable retainer from 0.028 to 0.032 inch (0.711-0.812 mm) diameter single strand round orthodontic spring wire arcuately curved in a general U-shape to describe an arch in the plane of and conforming to the arch of a patient's cuspid and incisor teeth. The respective end portions of the wire are offset inwardly, as at 12, so that the arch wire will adapt to the lingual contour of all the mandibular incisors and mandibular cuspids. This contoured arch wire 10 is bent medially its length to form one laterally directed transverse closed loop 14 at mesial-lingual surfaces of the mandibular central incisors. The term "closed loop" means that the wire is doubled back upon itself in U-shaped return bend fashion in which the legs defining the U-shape are in juxtaposition thus eliminating all spacing therebetween. The transverse closed loop 14 is three to five mm in length and is angulated downwardly 40° to 45° in a lingual direction with respect to a plane normal to the plane of the arch wire, as illustrated at A (FIG. 3). Each end 12 of the contoured arch wire 10 is attached to a conventional orthodontic band 16, as by a solder joint, or an orthodontic direct bond pad, not shown.

Figure 2:
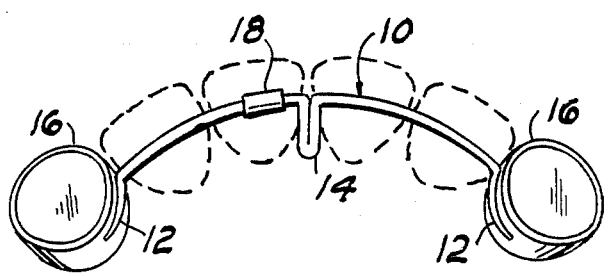
FIG. 2 is a view similar to FIG. 1, to an enlarged scale.

Once the fixed orthodontic adjustable arch wire retainer 10 is in the mouth, it is manifest that by the addition of round tubes or split sleeves 18 (FIG. 2), as presently explained, the adjustable retainer can supply additional force to correct and retain the teeth in a better alignment. It is quite easy to adjust this retainer to correct one or more teeth in this manner and not disturb the retention of the other teeth. The flexibility of this retainer, achieved by torsion provided by the closed loop 14, results in it being easy to insert and adapt to the abutment teeth of a patient.

The dual transverse loop embodiment 110 (FIG. 2) is formed similar to the embodiment 10 in which the central closed loop is omitted. A similarly formed left transverse closed loop 115 is positioned at the mesial edge of the left cuspid 20 and the distal edge of the left lateral incisor 22, as viewed in the drawings. The right transverse closed loop 115' is at the mesial edge of the right cuspid 24 and the distal edge of the right lateral incisor 26. These transverse closed loops are also three to five 5 mm in length and they are similarly angulated 40° to 60°. The contoured arch wire 110 is similarly attached to orthodontic bands 116 or an orthodontic direct bond pad.

Figure 5:
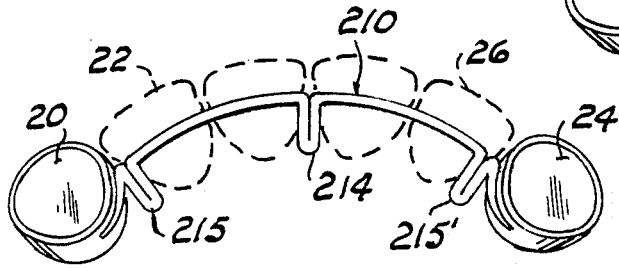

In the three transverse loop embodiment 210 (FIG. 5) the left transverse closed loop 215, as viewed in the drawings, is similarly disposed at the mesial edge of the left cuspid 20 and the distal edge of the left lateral incisor 22. The center transverse closed loop 214 is similarly disposed at the mesial-lingual surfaces of the mandibular central incisors. The right transverse closed loop 215' is disposed at the mesial edge of the right cuspid 24 and the distal edge of the right lateral incisor 26. The three transverse closed loops are similarly three to five mm in length and are similarly angulated 40° to 60°.

OPERATION

In use, the single, dual or three transverse loop arch wire embodiment is chosen in accordance with the desired flexibility of the retainer for correcting the position of the patient's teeth.

In actual practice a casting of the patient's mandibular dental arch is formed in a conventional manner and used to arcuately curve the arch wire. The respective end portions of the arch wire are secured to the cuspid surrounding band 16. The selected single, dual or triple closed loops are formed in the arch wire prior to the rigid connection of its connected end portions 12 to the bands 16. The preformed arch wire is then placed on the teeth of the patient.

Figure 6:
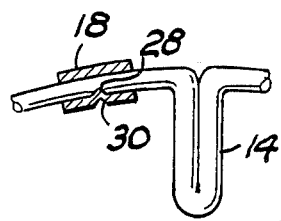

As an example and as illustrated by FIG. 6, the split sleeve 18 is positioned around the arch wire adjacent the central closed loop 14 at a selected position with respect to the left central incisor tooth, as viewed in the drawings. Prior to the placement of the sleeve 18, the arch wire is provided with a V-shaped indentation 28 in its surface with the V-shape extending transversely of the central axis of the arch wire. This indentation is formed in any conventional manner as by the cutting jaw of wire pliers, not shown. With the split sleeve 18 in position around the arch wire and the V-shaped notch 28 intermediate the wall length of the sleeve, the wall of the sleeve 18 is forcibly crimped inwardly into the notch 28, as at 30, to maintain the sleeve is a selected proper tooth contacting position with respect to the adjacent tooth and to prevent longitudinal movement of the sleeve relative to the arch wire.

The embodiment 10 is more flexible than an arch wire without a loop or loops therein. The embodiment 110 is more flexible than the embodiment 10 and the embodiment of 210 is more flexible than either of the other two embodiments. "Flexible" means the ability to manually move an intermediate portion of the wire in a lingual direction while remaining anchored at its flexible ends to the cuspids.

The principal advantage of the single or multiple closed loops of the respective embodiment is the ease of movement of the arch wire in a lingual direction on either side of the central loop 14 in the embodiment 10 and between the loops 115–115' in the embodiment 110 and between the closed loops 214 and 215–215' in the embodiment 210 by the torsional resistance of the arch wire at the return bend end of the respective loop. This torsional resistance is the force applied to the teeth or to a specific tooth following the application of one or more of the split sleeves 18.

The arch wire is primarily a retainer for teeth which maybe activated for moving a tooth or teeth which, after achieving the desired position for the tooth or teeth, the arch wire reverts to a tooth retainer maintaining the repositioned tooth or teeth in the desired position.

Obviously the invention is susceptible to changes or alterations without defeating its practicability. Therefore, I do not wish to be confined to the preferred embodiment shown in the drawings and described herein.

I claim:

1. An orthodontic mandibular arch wire for use with orthodontic bands or bonding pads, comprising:
    a unitary spring wire section substantially U-shaped in the plane of the natural dental arch and having its opposing end portions for connecting to a pair of orthodontic bands or bonding pads secured to a patient's cuspids;
    at least one transverse closed loop extending laterally and offset from the plane of said U-shaped wire so as to extend in a lingual direction and being located intermediate the ends of said wire section for permitting flexing movement in a lingual direction of intermediate portions of said wire section; and,
    means interposed between said wire section and a selected tooth of a patient's mandibular dental arch for moving said selected tooth relative to the adjacent teeth by the torsional resistance of that portion of the wire section forming the closed loop.

2. The arch wire according to claim 1 in which the respective end portion of said arch wire is offset inwardly for ease of its connection with the orthodontic band or bonding pad.

3. The arch wire according to claim 1 in which a pair of said closed loops are respectively disposed adjacent the opposing end portions of said arch wire.

4. The arch wire according to claim 1 in which said closed loop projects downwardly at an angle not less than 40° or greater than 60° with respect to a plane normal to the plane of the arch wire.

5. The arch wire according to claim 3 in which each loop of said pair of closed loops projects downwardly at an angle not less than 40° or greater than 60° with respect to a plane normal to the plane of the arch wire.

6. The arch wire according to claim 1 and further including:
    a split sleeve surrounding said arch wire at a selected location relative to a tooth to be moved; and,
    means securing said sleeve to the arch wire.

7. The arch wire according to claim 6 in which the arch wire is provided with a transverse V-shaped recess at the selected sleeve surrounding position and said securing means includes:
    an indentation in the wall of said sleeve disposed in the V-shaped recess.

* * * * *